US009339638B2

(12) United States Patent
Kang

(10) Patent No.: US 9,339,638 B2
(45) Date of Patent: May 17, 2016

(54) ANTIBIOTIC DELIVERY SYSTEM AND METHOD

(71) Applicant: HealthPartners Research & Education, Minneapolis, MN (US)

(72) Inventor: Matthew M. Kang, Minneapolis, MN (US)

(73) Assignee: HealthPartners Research & Education, Minneapolis, MN (US)

( * ) Notice: Subject to any disclaimer, the term of this patent is extended or adjusted under 35 U.S.C. 154(b) by 0 days.

(21) Appl. No.: 13/828,087

(22) Filed: Mar. 14, 2013

(65) Prior Publication Data
US 2014/0046273 A1  Feb. 13, 2014

Related U.S. Application Data

(60) Provisional application No. 61/680,741, filed on Aug. 8, 2012.

(51) Int. Cl.
*A61M 35/00* (2006.01)
*A61J 3/02* (2006.01)
(Continued)

(52) U.S. Cl.
CPC .............. *A61M 35/003* (2013.01); *A45D 33/02* (2013.01); *A61J 3/02* (2013.01); *A61M 13/00* (2013.01);
(Continued)

(58) Field of Classification Search
CPC .............. A61M 35/003; A61M 13/00; A61M 2202/0468; A61M 2202/064; A61M 2202/066; A45D 33/02; A61J 3/02; A47G 19/24; B65D 83/06; B65D 77/048; B65D 83/0481; A47J 42/12; A47J 42/14; A47J 42/18; A47J 42/20; A47J 42/32; A47J 42/34; A47J 43/22; A01C 15/00; A01C 15/02;
A01C 21/00; A01C 21/002; A01C 23/027; B05B 7/14; B05B 7/1404; B05B 7/1413; B05B 17/00; B05B 11/045; A61L 2300/406
USPC ................... 604/58, 59, 60; 222/189.02, 565; 53/205; 514/951
See application file for complete search history.

(56) References Cited

U.S. PATENT DOCUMENTS 1,542,430 A * 6/1925 Wever ...................... 222/189.04
1,878,924 A * 9/1932 Henry ........................... 366/130
(Continued)

FOREIGN PATENT DOCUMENTS

DE    2143599         3/1973
EP    0526706 A3 *    2/1993
FR    2863503          6/2005

OTHER PUBLICATIONS

O'Neill, Kevin R. M.D. et al., "Reduced surgical site infections in patients undergoing posterior spinal stabilization of traumatic injuries using vancomycin powder", The Spinal Journal 11, (2001) 641-646.
(Continued)

*Primary Examiner* — Adam Marcetich
(74) *Attorney, Agent, or Firm* — Barnes & Thornburg LLP

(57) ABSTRACT

The invention provides a system and method for delivering antibiotic powder to a surgical wound that reduces the likelihood of contamination. A pre-packaged, sterile antibiotic powder delivery system comprises a container; a measured dosage of an antibiotic powder disposed within the container; and a sieve top attached to the top of the container, wherein the container and sieve top are sealed as a unit in a sterile packaging. To use the delivery system in the sterile surgery or operating room environment, the delivery system is removed from the sterile packaging. The delivery system is shaken over the surgical wound for a reasonable amount of time to cover the entire wound, avoid surgeon fatigue at the end of surgery, and avoid prolonging the total time the wound is open.

10 Claims, 4 Drawing Sheets

(51) Int. Cl.
   *A45D 33/02*   (2006.01)
   *A61M 13/00*   (2006.01)
   A61L 15/44    (2006.01)
   A47G 19/34    (2006.01)
   A47G 19/24    (2006.01)

(52) U.S. Cl.
   CPC ............... *A47G 19/24* (2013.01); *A47G 19/34* (2013.01); *A61L 15/44* (2013.01); *A61L 2300/404* (2013.01); *A61L 2300/406* (2013.01); *A61M 2202/0468* (2013.01); *A61M 2202/064* (2013.01); *A61M 2202/066* (2013.01)

(56) References Cited

U.S. PATENT DOCUMENTS

| | | | |
|---|---|---|---|
| 2,470,298 A * | 5/1949 | Fields | 128/203.15 |
| 2,534,636 A | 12/1950 | Stirn | |
| 2,672,144 A | 3/1954 | Cohen | |
| 3,682,558 A * | 8/1972 | Miller | 401/200 |
| 3,761,590 A * | 9/1973 | Fox, Jr. | 514/157 |
| 5,634,900 A | 6/1997 | Makino et al. | |
| 6,060,461 A * | 5/2000 | Drake | 514/54 |
| 6,106,495 A | 8/2000 | Scott | |
| 6,247,661 B1 * | 6/2001 | Chainani | 241/169.1 |
| 6,306,119 B1 | 10/2001 | Weber et al. | |
| 6,468,253 B1 * | 10/2002 | Rucinski | 604/290 |
| 6,971,383 B2 | 12/2005 | Hickey et al. | |
| 7,455,248 B2 | 11/2008 | Kablik et al. | |
| 8,157,772 B2 | 4/2012 | Lewis | |
| 2005/0220721 A1 | 10/2005 | Kablik et al. | |
| 2007/0164060 A1 * | 7/2007 | Hayday | 222/633 |
| 2007/0194056 A1 * | 8/2007 | Webster | G01F 11/46 222/370 |
| 2008/0262417 A1 | 10/2008 | Kendall et al. | |
| 2009/0005734 A1 | 1/2009 | Herbette et al. | |
| 2009/0134256 A1 * | 5/2009 | Rice | 241/169.1 |
| 2009/0175926 A1 * | 7/2009 | Adams | 424/443 |
| 2010/0276441 A1 * | 11/2010 | Pordy et al. | 222/1 |
| 2011/0178495 A1 | 7/2011 | Ji | |
| 2011/0251580 A1 | 10/2011 | Greenhalgh et al. | |
| 2011/0288507 A1 * | 11/2011 | Rucinski | 604/290 |
| 2012/0286081 A1 * | 11/2012 | Delbridge et al. | 241/169.1 |
| 2013/0012893 A1 | 1/2013 | Smyth et al. | |

OTHER PUBLICATIONS

ClinicalTrials.gov, "Comparative Effectiveness and Cost-Benefit Analysis of Vancomycin Powder in High Risk Spine Surgery Patients", Jun. 2012.

* cited by examiner

ANTIBIOTIC DELIVERY SYSTEM AND METHOD

CROSS-REFERENCE TO RELATED APPLICATIONS

This application claims priority to provisional patent application, U.S. Application Ser. No. 61/680,741, entitled "Antibiotic Delivery System and Method," filed Aug. 8, 2012 and which is hereby incorporated by reference in its entirety.

BACKGROUND

The present application relates to the field of antibiotic delivery systems. More particularly, the application relates to the delivery of antibiotic powder during surgery, such as orthopedic surgery, spinal surgery, cardiovascular surgery, craniotomies, and other major surgeries, to reduce the need for revision surgery.

Delivering an antibiotic powder (such as Vancomycin) directly into a surgical wound prior to closure is a relatively novel concept. When applied during surgical procedures such as spinal surgery, delivery of an antibiotic powder has been shown to dramatically decrease the number of reoperations for deep spinal infections. This result has been shown in several major scientific articles, including "Intrawound Application of Vancomycin for Prophylaxis in Instrumented Thoracolumbar Fusions," SPINE, Vol. 36, No. 24, pp. 2084-2088 (2011) and "Reduced Surgical Site Infections in Patients Undergoing Posterior Spinal Stabilization of Traumatic Injuries Using Vancomycin Powder," The Spine Journal, Vol. 11, pp. 641-646 (2011). In these "case versus control" studies, there were significant differences in post-operative infections requiring an operation to treat the infection depending on the use of antibiotic powder directly into the surgical wound. The use of an antibiotic powder leads to lower operative infection rates. The low potential for developing resistance due to poor systemic uptake of the antibiotic and lack of side effects makes the use of antibiotic powder directly into surgical wounds very appealing. The cost savings to the healthcare system by using a fairly inexpensive antibiotic is tremendous as revision surgery, at least for spinal surgeries, can cost several hundreds of thousands of dollars per instance.

Current methods of delivering antibiotic powders locally to the surgical wound have had a high potential for contamination and are inefficient, leading to wasted time in the operating room. Typically, a non-sterily gowned person (e.g. anesthesiologist or circulating nurse) pours the antibiotic powder using a non-sterile technique into some type of open sterile plastic container. This container is held by a sterile scrubbed person (e.g. the surgeon or scrub nurse). This individual must further crush the antibiotic powder. After the powder is crushed it is sprinkled into the wound by grasping some of the crushed powder by hand and then releasing into the wound. There are numerous points of potential contamination and accidental spilling that can occur in this process, and this method may be imprecise in terms of the quantity of powder present in the open wound.

Some prior delivery devices for antibiotic powders require attaching a prepared vial of antibiotic powder to a delivery device, which does not necessarily correct the deficiencies of the methods described above. In addition, these prior art delivery devices use pressurized gas or liquid that effectively aerates the powder or turns it into an aerosol to dispense the antibiotic powder into the wound, which may affect the efficacy of the dosage of the antibiotic.

Accordingly, there exists a need for a powder delivery device that is self-contained to reduce the potential for contamination and that allows for a practitioner to dispense a desired amount of the powder into a surgical wound.

BRIEF SUMMARY OF THE INVENTION

The present invention is a pre-packaged, sterile antibiotic powder delivery system and methods for making and using the system.

In at least one embodiment, the pre-packaged, sterile antibiotic powder delivery system comprises a container having a generally cylindrical body with a bottom, a sidewall extending upwardly from the bottom and a mouth at the top of the container; a measured dosage of an antibiotic powder disposed within the container; and a sieve top attached to the mouth of the container, the sieve top having a plurality of holes with a diameter. In some embodiments, a small handle is attached to the sidewall of the container or the sieve top to improve control and securely grasp the device during administration of the drug. The container, with the measured dosage disposed within the container, and the sieve top attached to the mouth of the container are sealed as a unit in a sterile packaging. In at least one embodiment, the sieve top is removably attached to the mouth of the container. In at least one embodiment, the sieve top has a plurality of threads and the mouth of the container has a plurality of threads such that the sieve top can be threadably engaged with the mouth of the container. In at least one embodiment, the diameter of the plurality of holes is adjustable. In at least one embodiment, the antibiotic powder is crushed before it is disposed within the container. In some embodiments, a grinding mechanism is disposed within the container to crush the powder, or in the case where the antibiotic powder is crushed before it is disposed within the container, the grinding mechanism may be used to crush the powder to a finer grain size. In some embodiments, the sieve top further comprises a grinding mechanism. In at least one embodiment, a removable cap that is disposed over the mouth of the container and the sieve top.

A method of manufacturing the antibiotic powder delivery system comprises disposing an amount of antibiotic powder into a sterile container, the sterile container having a generally cylindrical body with a bottom, a sidewall extending upwardly from the bottom and a mouth at the top of the container; attaching a sterile sieve top to the mouth of the container to form a delivery system; sealing the delivery system in sterile packaging. In some embodiments, the amount of antibiotic powder is equivalent to a single dosage. In some embodiments, the method further comprises attaching a sterile cap over the sterile sieve top before sealing the delivery system in the sterile packaging.

A method of dispensing a dosage of antibiotic powder into a surgical wound comprises removing a delivery system from sterile packaging, the delivery system comprising a container having a generally cylindrical body with a bottom, a sidewall extending upwardly from the bottom and a mouth at the top of the container; a measured dosage of an antibiotic powder disposed within the container; and a sieve top attached to the mouth of the container, the sieve top having a plurality of holes with a diameter; and shaking the delivery system over the surgical wound for a period of time such that the antibiotic powder is dispensed through the sieve top and into the surgical wound.

The figures and the detailed description which follow more particularly exemplify these and other embodiments of the invention.

DETAILED DESCRIPTION OF THE INVENTION

Figure 1:
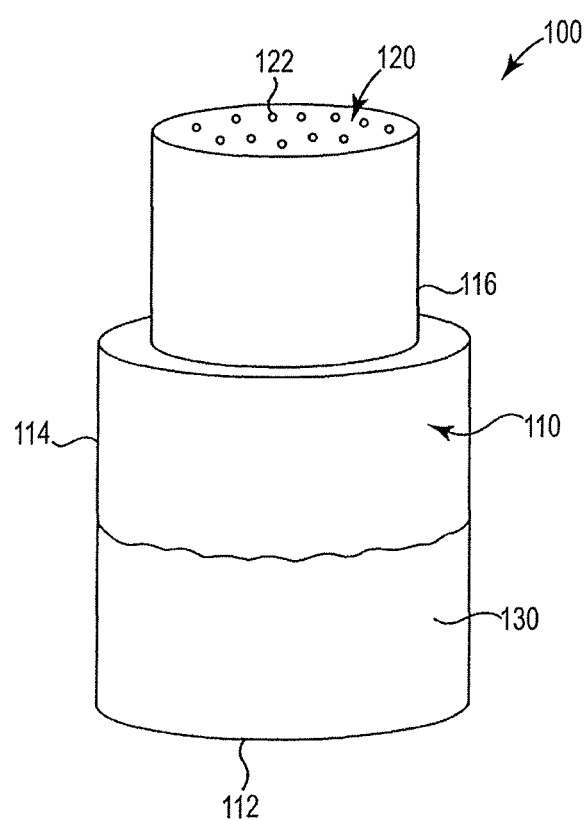
FIG. 1 is a perspective view of an embodiment of an antibiotic powder delivery system.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

FIG. 1 shows an embodiment of a pre-packaged, sterile antibiotic powder delivery system 100 of the present invention. In at least one embodiment, the antibiotic powder delivery system includes a powder container 110, a sieve top 120, and a pre-measured dosage of antibiotic powder 130. The powder container 110 is a generally cylindrical body having a bottom 112, a sidewall 114 extending upwardly from the bottom 112, and an open mouth 116 at the top of the container 110. In at least one embodiment, the mouth 116 may be at a reduced diameter portion of the container 110 The sieve top 120 is attached to the powder portion 110 at the open mouth 116 of the container 110. In at least one embodiment, the sieve top 120 is removably attached to the container 110. In at least one embodiment, the sieve top 120 is disposed within the open mouth 116 of the container 110. In some embodiments, the sieve top 120 may have a plurality of threads that match threads on an outer surface of the open mouth 116, so that the sieve top 120 can be threadably engaged with the open mouth 116. The sieve top 120 has a plurality of holes 122. In at least one embodiment, the diameter of the holes 122 have a specific diameter that is carefully selected in connection with the desired particle size or grain size of the antibiotic powder 130 so as to allow even administration of the antibiotic powder that is not too rapid or too slow. In some embodiments, the diameter of the holes 122 is less than 0.5 mm. In some embodiments, the diameter of the holes 122 is less than 100 microns. In one embodiment, the diameter of the holes 122 is between about 60 microns and 80 microns. In a preferred embodiment, the diameter of the holes 122 is between about 10 microns and 50 microns. In some embodiments, the holes 122 all have the same diameter and in other embodiments the holes 122 have different diameters. In at least one embodiment, a pre-measured dosage of antibiotic 130, such as Vancomycin, is provided within the powder container portion 110. In some embodiments, the antibiotic 130 may be pre-crushed into a fine powder before it is provided within the powder container portion 110. In at least one embodiment, the powder container portion 110 and sieve top 120 are sterilized, and then the antibiotic 130 is added to the container 110 in a sterile environment. The sieve top is then attached to the container 110, and the entire delivery system is then sealed in a sterile packaging. Hence, there is no direct handling of the antibiotic powder or the delivery container by non-sterilely gowned personnel. In addition, the pre-packaged, sterile antibiotic powder delivery system with the pre-measured dosage of antibiotic 130 can be a single use system, meaning that none of the elements of the delivery system are reused. This further reduces the potential for future contamination or insufficient dosage, thus increasing the efficacy of the antibiotic treatment.

In some embodiments, the sieve top 120 comprises a plurality of adjustable sized holes, which allows the practitioner to provide a coarser or finer grain size. In some embodiments, the sieve top 120 comprises a plurality of discs with holes of various diameters. The practitioner may then select one of the discs of a desired hole diameter, for example by rotating the sieve top 120 In another embodiment, the diameter of the holes 122 of the sieve top 120 is not a fixed diameter and may be adjusted by the practitioner by rotation of the sieve top 120 or other means. This allows the practitioner some flexibility in selecting a coarser or finer grain size for the antibiotic 130.

Figure 2:
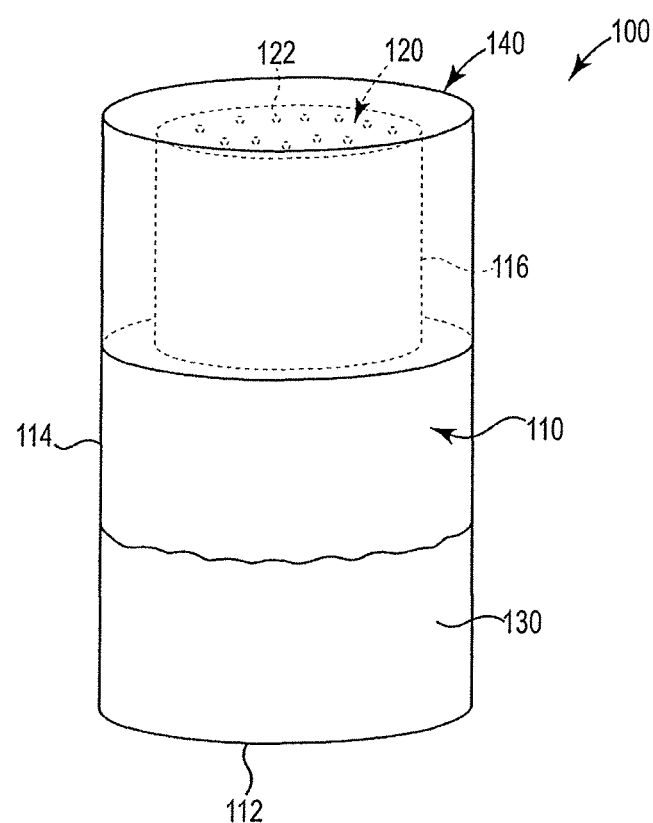
FIG. 2 is a perspective view of an embodiment of an antibiotic powder delivery system.

In at least one embodiment, as shown in FIG. 2, the antibiotic powder delivery system may further include a removable cap 140, which is disposed over the open mouth 116. In at least one embodiment, the cap 140 may have a plurality of threads that match threads on an outer surface of the open mouth 116, so that the cap 140 can be threadably engaged with the open mouth in order to close the container. In one embodiment, the cap 140 may form an interference fit or friction fit with the mouth 116 in order to close the container. In at least one embodiment, the cap 140 covers the sieve top 120, which is disposed within the mouth 116 of the container 110. In some embodiments, the cap 140 which closes the container and the sieve top 120 are integrally formed into a cap-sieve top assembly. In at least one embodiment, by rotating the cap-sieve top assembly, the practitioner can open or close the container 110 and, in some embodiments, the practitioner can also select the diameter of the holes 122. Including a cap to close off the antibiotic stored in the container from environmental effects can further reduce the potential for future contamination.

Figure 3:
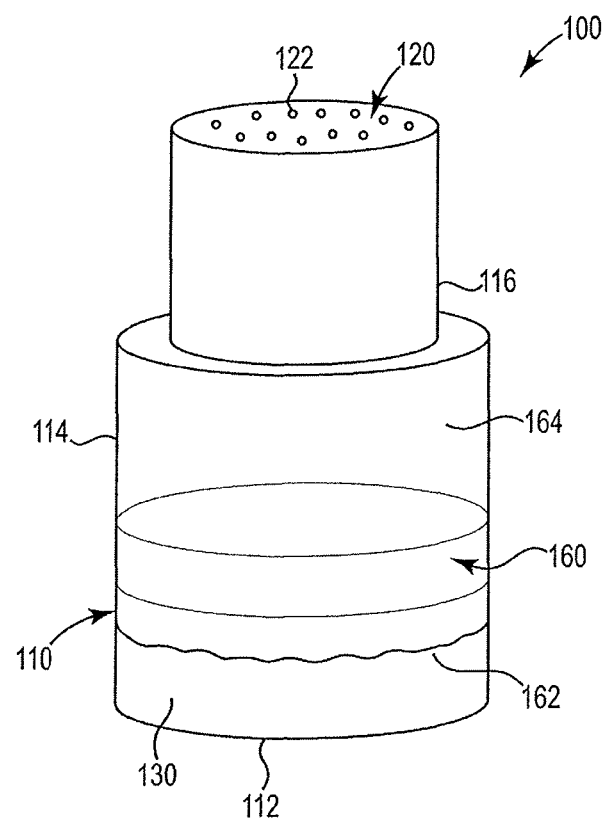
FIG. 3 is a perspective view of an embodiment of an antibiotic powder delivery system.

While, as discussed above, the antibiotic powder 130 may be pre-crushed into a desired grain size or particle size before it is deposited into the container 110, in some embodiments, the antibiotic powder delivery system 110 may comprise a grinding mechanism 160 that when activated can crush the antibiotic powder into a smaller, desired grain size or particle size. As shown in FIG. 3, the antibiotic powder delivery system further comprises a grinding mechanism, shown generally at 160, disposed within the container 110. In one embodiment, the grinding mechanism 160 is formed with the container 110 and is not removable, and in other embodiments, the grinding mechanism 160 may be removably disposed within the container 110. The grinding mechanism 160 may be similar to, for instance, a pepper mill where rotation of an outer portion of the container (such as the sidewall 114) activates the grinding mechanism 160. In other embodiments, the grinding mechanism 160 may comprise a plurality of weighted balls disposed within the container 110 whereby shaking the container vigorously (with the cap in place) causes the balls to further crush the powder into a finer grain. In at least one embodiment, the grinding mechanism 160 is adjustable to provide varying degrees of grain size or particle size as needed. In at least one embodiment, the grinding mechanism 160 may be selected to produce a coarse grain size or a fine grain size. In at least one embodiment, the grinding mechanism 160 separates the container into a pre-crushed portion 162 between the bottom 112 and the grinding mechanism 160, and a post-crushed portion 164 between the grinding mechanism 160 and the sieve top 120, wherein the antibiotic powder 130 is initially disposed within the pre-crushed portion 162. In at least one embodiment, the bottom 112 is removably attached to the sidewall 114 of the container 130, and when removed, the antibiotic powder 130 can be disposed within the pre-crushed portion 162. In some embodiments, the grinding mechanism 160 is integrally formed with the sieve top 120 so that the sieve top 120 both crushes the antibiotic powder into a desired grain size and dispenses the crushed antibiotic powder. In at least one embodiment, the powder container portion 110, the grinding mechanism 160 and sieve top 120 are sterilized, and then the antibiotic 130 is added to the pre-crushed portion 162 of the container 110 in a sterile environment. The sieve top 120 is then attached to the container 110, and the entire delivery system is then sealed in a sterile packaging. In use, the grinding mechanism 160 is activated to crush the antibiotic powder, which is then dispensed through the holes 122 in the sieve top 120. This way, there is no direct handling of the antibiotic powder or the delivery container by non-sterilely gowned personnel. In addition, there is no direct handling of the antibiotic powder either during the crushing process or the dispensing process.

Figure 4:
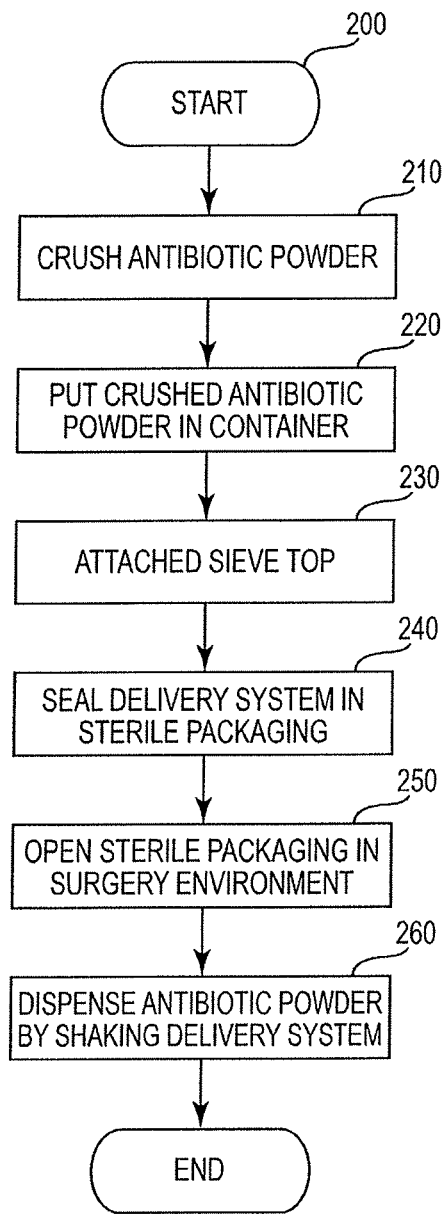
FIG. 4 is a flow chart showing a method for delivering antibiotic powder to a surgical wound.

One method 200 of making and using the delivery system 100 is shown in FIG. 4. The method described herein preferably should be accomplished within a sterile environment, such as in a pharmaceutical lab or manufacturing facility. The method starts at step 210 by crushing an antibiotic powder 130, such as Vancomycin. The antibiotic 130 should be crushed such that the grain size of the antibiotic 130 is appropriately sized for distribution within a surgical wound environment. At step 220, the crushed antibiotic 130 is placed into a sterile container 110. While the method shown in FIG. 4 begins by crushing the antibiotic powder before disposing it into a sterile container 110, in some embodiments where a grinding mechanism 160 is provided, the antibiotic powder can be disposed within the container 110 before it is crushed. In at least one embodiment, the amount of antibiotic 130 added to the container 110 should be a single therapeutically effective dosage to be used in a surgical procedure. For Vancomycin, when used in spinal surgery, the therapeutically effective dosage should be between 1 and 2 grams. A sterile sieve top 120, as described above, is then attached to the container 110 at step 230. In some embodiments a cap 140 may also be attached to ensure that the container 110 is closed. The delivery system 100 is then sealed in sterile packaging at step 240. This completes the method of manufacturing the delivery system.

To use the delivery system in the sterile surgery or operating room environment, the delivery system 100 is removed from the sterile packaging at step 250. Where the cap 140 is used, the cap may first be removed. At step 260, to deliver the entire dosage of the antibiotic 130 to a surgical wound, the delivery system is shaken over the surgical wound for a reasonable amount of time to cover the entire wound, avoid surgeon fatigue at the end of surgery, and avoid prolonging the total time the wound is open. In at least one embodiment, the total time should not exceed two minutes, and is preferably between about one to two minutes. In at least one embodiment, the delivery system is shaken over the surgical wound for between about fifteen seconds and one minute. In at least one embodiment, the delivery system is shaken over the surgical wound for between about fifteen and thirty seconds.

Generally, the antibiotic 130 is merely delivered by the force exerted by shaking the delivery system and gravity extracting the antibiotic 130 from the delivery device 100. In other words, there is no pressurized gas or fluid applied to the delivery device 100 in order to deliver the antibiotic 130. In some embodiments, the delivery device 100 may be adapted to use pressurized gas or fluid to extract the antibiotic 130 from the container 110 and through the holes 122 in the sieve top 120 by introducing pressurized gas or fluid to the container 110 through a port in the sidewall 114 of the container 110.

Although the embodiments described herein may reference only spinal surgery, the delivery device 100 is applicable for all surgeries, including orthopedic, oral, cardiovascular, neurosurgery, spinal, abdominal, endocrine, oncological, and urological. In addition, although the embodiments described herein may reference Vancomycin, any other suitable antibiotics may be used in powder form. The applicable dosage and grain size depends on the type of surgery and the selected antibiotic.

In some embodiments, a small handle is attached to the sidewall of the container or the sieve top to improve control and securely grasp the device during administration of the drug.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A pre-packaged, sterile antibiotic powder delivery system consisting of:
    a sterilized container having a generally cylindrical body with a bottom, a sidewall extending upwardly from the bottom and a mouth at the top of the container;
    a pre-measured single therapeutically effective dosage of an antibiotic powder disposed within the container;
    a sterilized sieve top attached to the mouth of the container, the sterilized sieve top comprising a selected one of a plurality of discs, each of the plurality of discs comprising holes having a diameter; and
    a sterilized removable cap that is disposed over the mouth of the container and the sieve top,
    wherein the container with the pre-measured dosage disposed within the container and the sieve top attached to the mouth of the container are sealed as a unit in a sterile packaging and the container with the pre-measured dosage is removed from the sterile packaging in preparation for use;
    wherein the pre-measured dosage of the antibiotic powder comprises a grain size that, in combination with diameter of the holes in the selected one of the plurality of discs, allows full shaking delivery of the single therapeutically effective dosage of the antibiotic powder from the container within a time range of less than 2 minutes.

2. The antibiotic powder delivery system of claim 1, wherein the sieve top is removably attached to the mouth of the container.

3. The antibiotic powder delivery system of claim 2, wherein the sieve top has a plurality of threads and the mouth of the container has a plurality of threads such that the sieve top can be threadably engaged with the mouth of the container.

4. The antibiotic powder delivery system of claim 1, wherein the diameter of the holes in the selected disc is less than 0.5 mm.

5. The antibiotic powder delivery system of claim 1, wherein the diameter of the holes in the selected disc is less than 100 microns.

6. The antibiotic powder delivery system of claim 1, wherein the diameter of the holes in the selected disc is between about 60 microns and 80 microns.

7. The antibiotic powder delivery system of claim 1, wherein the diameter of the holes in the selected disc is between about 10 microns and 50 microns.

8. The antibiotic powder delivery system of claim 1, wherein the antibiotic powder is crushed before it is disposed within the container.

9. The antibiotic powder delivery system of claim 1, further comprising:
   a grinding mechanism disposed within the container to crush the powder, the grinding mechanism comprising a plurality of weighted balls disposed within the container.

10. The antibiotic powder delivery system of claim 1, wherein the sieve top further comprises a grinding mechanism.

* * * * *